(12) United States Patent
Beatch et al.

(10) Patent No.: US 7,053,087 B1
(45) Date of Patent: May 30, 2006

(54) AMINOCYCLOALKYL CINNAMIDE COMPOUNDS FOR ARRHYTHMIA AND ANALGESICS AND ANESTHETICS

(75) Inventors: Gregory N. Beatch, Vancouver (CA); Cindy J. Longley, Vancouver (CA); Michael J. A. Walker, Vancouver (CA); Richard A. Wall, Vancouver (CA)

(73) Assignee: Cardiome Pharma Corp., Vancouver (CA)

( * ) Notice: Subject to any disclaimer, the term of this patent is extended or adjusted under 35 U.S.C. 154(b) by 0 days.

(21) Appl. No.: 09/914,884

(22) PCT Filed: Mar. 3, 2000

(86) PCT No.: PCT/CA00/00217

§ 371 (c)(1),
(2), (4) Date: Feb. 26, 2002

(87) PCT Pub. No.: WO00/51981

PCT Pub. Date: Sep. 8, 2000

Related U.S. Application Data

(60) Provisional application No. 60/122,858, filed on Mar. 4, 1999.

(51) Int. Cl.
*A61K 31/5375* (2006.01)
*C07D 295/155* (2006.01)

(52) U.S. Cl. .................. 514/237.8; 544/166
(58) Field of Classification Search ............. 514/237.8; 544/168
See application file for complete search history.

(56) References Cited

U.S. PATENT DOCUMENTS

| | | | |
|---|---|---|---|
| 4,179,501 A | 12/1979 | Szmuszkovicz | 424/226 |
| 4,598,087 A | 7/1986 | Horwell | 514/429 |
| 4,656,182 A | 4/1987 | Horwell | 514/324 |
| 4,663,343 A | 5/1987 | Horwell et al. | 514/429 |
| 5,051,428 A | 9/1991 | Horwell et al. | 514/320 |
| 5,506,257 A * | 4/1996 | MacLeod et al. | 514/422 |

FOREIGN PATENT DOCUMENTS

| | | | |
|---|---|---|---|
| EP | 0222533 A1 | | 5/1987 |
| EP | 0380063 B1 | | 8/1990 |
| JP | 58-152876 | * | 9/1983 |
| WO | WO 93/19056 | | 9/1993 |

OTHER PUBLICATIONS

FDA mulls drup to slow late-stage Alzheimer's [online], [retrieved on Sep. 9, 2004], Retrieved from the Internet<URL:http://www.cnn.com/2003/HEALTH/conditions/09/24/alzheimers.drug.ap/index.html>.*

Stefan E. Boiadjiev et al., "pH-Sensitive Exciton Chirality Chromophor. Solvatochromic Effects On Circular Dichroism Spectra," *Tetrahedron: Asymmetry*, 7(10): 2825-2832, Oct. 1, 1996.

Brian R. de Costa et al., "Synthesis and Evaluation on N-Substituted cis-N-Methyl-2-(1-pyrrolidinyl) cyclohexylamines as High Affinity σ Receptor Probes," *J. Mem. Chem*, 33(11): 3100-3110, 1990.

* cited by examiner

*Primary Examiner*—Kamal A. Saeed
*Assistant Examiner*—Rebecca Anderson
(74) *Attorney, Agent, or Firm*—Seed IP Law Group PLLC

(57) ABSTRACT

Aminocycloalkyl cinnamide compounds (I) are disclosed. The compounds of the present invention may be incorporated in compositions and kits. The present invention also discloses a variety of in vitro and in vivo uses for the compounds and compositions, including the treatment of arrhythmia and the production of local analgesia and anesthesia. n=1–4; $R_1$, $R_2$, $R_3$, $R_4$, $R_5$, $R_{13}$, X and A are as in claim (1).

6 Claims, 1 Drawing Sheet

AMINOCYCLOALKYL CINNAMIDE COMPOUNDS FOR ARRHYTHMIA AND ANALGESICS AND ANESTHETICS

This application is a 371 of PCT/CA00/00217 filed 3 Mar. 2000.

This application claims the benefit of Provisional Application No. 60/122,858, filed Mar. 4, 1999.

TECHNICAL FIELD

The present invention is generally directed toward aminocycloalkyl cinnamide compounds, pharmaceutical compositions and kits containing the aminocycloalkyl cinnamide compounds, and therapeutic uses thereof.

BACKGROUND OF THE INVENTION

Arrhythmia is a variation from the normal rhythm of the heart beat and generally represents the end product of abnormal ion-channel structure, number or function. Both atrial arrhythmias and ventricular arrhythmias are known. The major cause of fatalities due to cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these will be first heart attacks and 450,000 will be recurrent attacks. About one-third of the people experiencing these attacks will die of them. At least 250,000 people a year die of coronary heart disease within 1 hour of the onset of symptoms and before they reach a hospital. These are sudden deaths caused by cardiac arrest, usually resulting from ventricular fibrillation.

Atrial fibrillation (AF) is the most common arrhythmia seen in clinical practice and is a cause of morbidity in many individuals Its prevalence is likely to increase as the population ages and it is estimated that 3–5% of patients over the age of 60 years have AF. While AF is rarely fatal, it can impair cardiac function and is a major cause of stroke.

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Nattel S., Hadjis T., Talajic M., *Drugs* 48(3):345–71, 1994). However, drug therapy is often limited by adverse effects, including the possibility of increased mortality, and inadequate efficacy (Nattel S., *Cardiovascular Research.* 37(3):567–77, 1998). Conversion rates for Class I antiarrhythmics range between 50–90% (Steinbeck G., Remp T., Hoffmann E., *Journal of Cardiovascular Electrophysiology.* 9(8 Suppl):S104–8, 1998). Class III antiarrhythmics appear to be more effective for terminating atrial flutter than for AF and are generally regarded as less effective than Class I drugs for terminating AF (Capucci A., Aschieri D., Villani G. Q., *Drugs &Aging* 13(1):51–70, 1998). Examples of such drugs include ibutilide, dofetilide and sotalol. Conversion rates for these drugs range between 30–50% for recent onset AF (Capucci A., Aschieri D. Villani G. Q., *Drugs &Aging* 13(1):51–70, 1998), and they are also associated with a risk of the induction of Torsades de Pointes ventricular tachyarrhythmias. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *American Journal of Cardiology* 78(8A):46–52, 1996). Such events are particularly tragic in the case of AF as this arrhythmia is rarely fatal in and of itself.

Therefore, there is a need in the art to identify new antiarrhythmic treatments, for both ventricular arrhythmias as well as for atrial arrhythmias. The present invention fulfills this need, and further provides other related advantages.

SUMMARY OF THE INVENTION

In one embodiment, the present invention provides aminocycloalkyl cinnamide compounds of formula (I), or a solvate or pharmaceutically acceptable salt thereof:

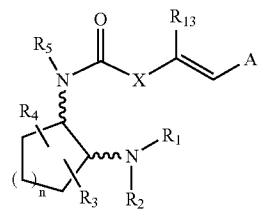

wherein, independently at each occurrence, n is selected from 1, 2, 3 and 4;

X is selected from a direct bond, and —C($R_6$,$R_{14}$)—Y—,

Y is selected from a direct bond, O, S, and $C_1$–$C_4$alkylene;

$R_{13}$ is selected from hydrogen, $C_1$–$C_6$alkyl, $C_3$–$C_8$cycloalkyl, aryl, and benzyl;

$R_1$ and $R_2$ are independently selected from hydrogen, $C_1$–$C_8$alkyl, $C_3$–$C_8$alkoxyalkyl, $C_1$–$C_8$hydroxyalkyl, and $C_1$–$C_{12}$aralkyl; or $R_1$ and $R_2$, when taken together with the nitrogen atom to which they are directly attached in formula (I), form a ring denoted by formula (II):

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may bear one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, $C_1$–$C_{20}$alkanoyloxy, or may form a Spiro five- or six-membered heterocyclic ring containing one or two heteroatoms selected from oxygen and sulfur; and any two adjacent additional carbon ring atoms may be fused to a $C_3$–$C_8$carbocyclic ring, and any one or more of the additional nitrogen ring atoms may bear substituents selected from hydrogen, $C_1$–$C_6$alkyl, $C_2$–$C_4$acyl, $C_2$–$C_4$hydroxyalkyl and $C_3$–$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cycloalkyl ring shown in formula (I) at other than the 1 and 2 positions and are independently selected from hydrogen, hydroxy, $C_1$–$C_6$alkyl and $C_1$–$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$–$C_6$alkyl, aryl and benzyl, or $R_6$ and $R_{14}$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (III), (IV), (V), (VI), (VII) and (VIII):

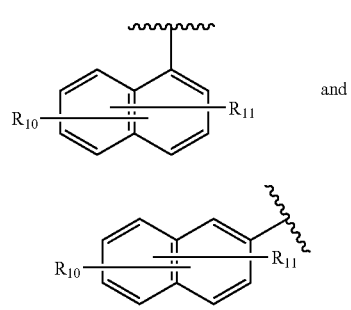

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl and $C_1$–$C_6$alkyl;

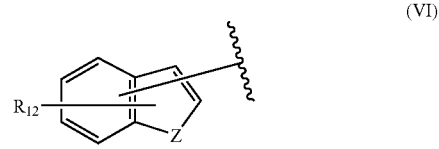

(IV) and (V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl;

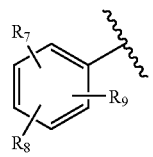

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and Z is selected from CH, $CH_2$, O, N and S, where Z may be directly bonded to the carbon atom in formula (I) that is shown directly bonded to "A" when Z is CH or N, or Z may be directly bonded to $R_{17}$ when Z is N, and $R_{17}$ is selected from hydrogen, $C_1$–$C_6$alkyl, $C_3$–$C_8$cycloalkyl, aryl and benzyl;

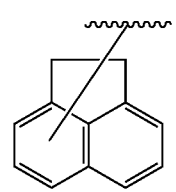

(VII)

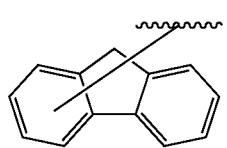

(VIII)

including isolated enantiomeric, diastereomeric and geometric isomers thereof, and mixtures thereof;

with the proviso that, said compound of formula (I) may not be (1R,2S)/(1S,2R)-N-methyl-N-[2-(1-pyrrolidinyl)cyclohexyl]-3,4-dichlorocinnamide.

In other embodiments, the present invention provides a composition or medicament that includes a compound according to formula (I) without the proviso in combination with a pharmaceutically acceptable carrier, diluent or excipient, and further provides a method for the manufacture of a composition or medicament that contains a compound according to formula (I) without the proviso.

In other embodiments, the present invention provides pharmaceutical compositions that contain at least one compound of formula (I) without the proviso in an amount effective to treat a disease or condition in a warm-blooded animal suffering from or having the disease or condition, and/or prevent a disease or condition in a warm-blooded animal that would otherwise occur, and further contains at least one pharmaceutically acceptable carrier, diluent or excipient. The invention further provides for methods of treating a disease or condition in a warm-blooded animal suffering from or having the disease or condition, and/or preventing a disease or condition from arising in a warm-blooded animal, wherein a therapeutically effective amount of a compound of formula (I) without the proviso, or a composition containing a compound of formula (I) without the proviso is administered to a warm-blooded animal in need thereof. The diseases and conditions to which the compounds, compositions and methods of the present invention have applicability are as follows: arrhythmia, diseases of the central nervous system, convulsions, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

In another embodiment, the present invention provides a pharmaceutical composition containing an amount of a compound of formula (I) without the proviso effective to produce local analgesia or anesthesia in a warm-blooded animal in need thereof, and a pharmaceutically acceptable carrier, diluent, or excipient. The invention further provides a method for producing, local analgesia or anesthesia in a warm-blooded animal which includes administering to a warm-blooded animal in need thereof an effective amount of a compound of formula (I) without the proviso or a pharmaceutical composition containing a compound of formula (I) without the proviso. These compositions and methods may be used to relieve or forestall the sensation of pain in a warm-blooded animal.

In another embodiment, the present invention provides a pharmaceutical composition containing an amount of a compound of formula (I) without the proviso effective to enhance the libido in a warm-blooded animal in need thereof, and a pharmaceutically acceptable carrier, diluent, or excipient. The invention further provides a method for enhancing libido in a warm-blooded animal which includes administering to a warm-blooded animal in need thereof an effective amount of a compound of formula (I) without the proviso or a pharmaceutical composition containing a compound of formula (I) without the proviso. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

In another embodiment, the present invention provides a compound of formula (I) without the proviso or composition containing a compound of formula (I) without the proviso, for use in methods for either modulating ion channel activity in a warm-blooded animal or for modulating ion channel activity in vitro.

These and other embodiments of the present invention will become evident upon reference to the following drawings and detailed description.

DETAILED DESCRIPTION OF THE INVENTION

Figure 1A:
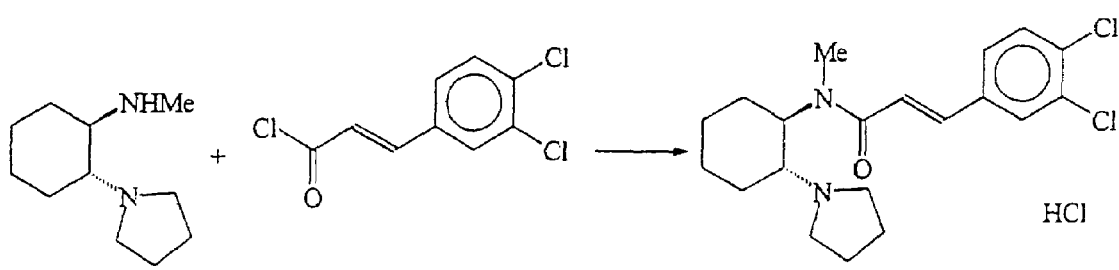
FIGS. 1A, 1B and 1C illustrates reaction sequences further described in Examples 1, 2 and 3, respectively, for preparing aminocycloalkyl cinnamide compounds of the present invention.

As noted above, the present invention is directed to aminocycloalkyl cinnamide compounds, pharmaceutical compositions containing the aminocycloalkyl cinnamide compounds, and various uses for the compound and compositions. Such uses include modulation of ion channels in vitro or in vivo, the treatment of arrhythmias, the production of anesthesia, and other uses as described herein. An understanding of the present invention may be aided by reference to the following definitions and explanation of conventions used herein.

Definitions and Conventions

The aminocycloalkyl cinnamide compounds of the invention have a cinnamide group

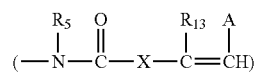

at position 1 of a cycloalkyl ring, and an amine nitrogen atom at position 2 of the cycloalkyl ring. The cycloalkyl ring is either cyclopentyl, cyclohexyl, cycloheptyl or cyclooctyl, with other positions numbered in corresponding order as shown below in structure (A) for cyclopentane, structure (B) for cyclohexane, structure (C) for cycloheptane, and structure (D) for cyclooctane:

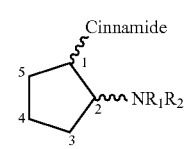

(A)

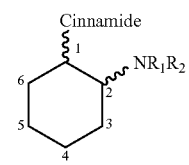

(B)

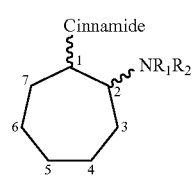

(C)

-continued

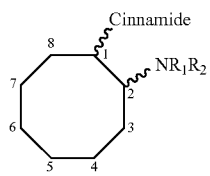
(D)

The bonds from the cycloalkyl ring to the 1-cinnamide and 2-amine groups in the above formula may be relatively disposed in either a cis or trans relationship. In a preferred embodiment of the present invention, the stereochemistry of the amine and cinnamide substituents of the cycloalkyl ring is either (R,R)-trans or (S,S)trans. In another preferred embodiment the stereochemistry is either (R,S)-cis or (S,R)-cis.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing the cinnamide group

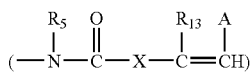

where A equals formula (III)

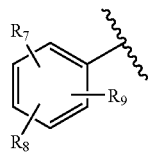
(III)

are intended to encompass compounds having the group (E) (where, for convenience, only one possible geometric isomer is shown):

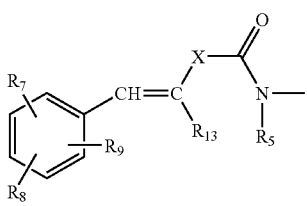
(E)

where the group (E) is intended to encompass groups wherein any ring atom that could otherwise be substituted with hydrogen, may instead be substituted with either $R_7$, $R_8$ or $R_9$, with the proviso that each of $R_7$, $R_8$ and $R_9$ appears once and only once on the ring. Ring atoms that are not substituted with any of $R_7$, $R_8$ or $R_9$ are substituted with hydrogen. In those instances where the invention specifies that a non-aromatic ring is substituted with more than one R group, and those R groups are shown connected to the non-aromatic ring with bonds that bisect ring bonds, then the R groups may be present at different atoms of the ring, or on the same atom of the ring, so long as that atom could otherwise be substituted with a hydrogen atom.

Likewise, where the invention specifies compounds containing the cinnamide group

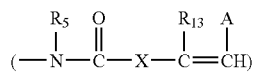

where A equals the aryl group (VI)

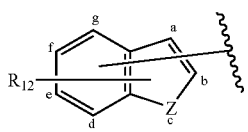
(VI)

the invention is intended to encompass compounds wherein

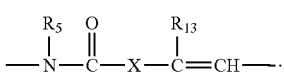

is joined through the single bond of =CH— to the aryl group (VI) at any atom which forms the aryl group (VI) so long as that atom of group (VI) could otherwise be substituted with a hydrogen atom. Thus, there are seven positions (identified with the letters "a" through "g") in structure (VI) where the =CH— group could be attached, and it is attached at one of those seven positions. The $R_{12}$ group would occupy one and only one of the remaining six positions, and hydrogen atoms would be present in each of the five remaining positions. It is to be understood that when Z represents a divalent atom, e.g., oxygen or sulfur, then Z cannot be directly bonded to

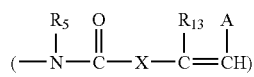

When the invention specifies the location of an asymmetric divalent radical, then that divalent radical may be positioned in any possible manner that provides a stable chemical structure. For example, for compounds containing the cinnamide group where X is C($R_{14}$,$R_6$)—Y—, the invention provides compounds having both the

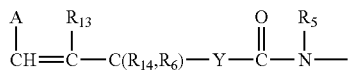

and

groups.

A wavy bond from a substituent to the central cycloalkyl ring indicates that the substituent may be located on either side of the plane of the central ring.

The compounds of the present invention contain at least two asymmetric carbon atoms and thus exist as enantiomers and diastereomers. Unless otherwise noted, the present invention includes all enantiomeric and diastereomeric forms of the aminocycloalkyl cinnamide compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers with all isomeric forms being included in the present invention. A racemate or racemic mixture does not imply a 50:50 mixture of stereoisomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents and/or variables are permissible only if such combinations result in stable compounds.

In accordance with the present invention and as used herein, the following terms are defined to have the following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C=O)— group containing the specified number of carbon atoms. Examples include acetyl [$CH_3C(=O)$—, a $C_2$acyl] and propionyl [$CH_3CH_2C(=O)$—, a $C_3$acyl].

"Alkanoyloxy" refers to an ester substituent wherein the non-carbonyl oxygen is the point of attachment to the molecule. Examples include propanoyloxy [($CH_3CH_2C(=O)$—O—, a $C_3$alkanoyloxy] and ethanoyloxy [$CH_3C(=O)$—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2C(=O)$—, a $C_3$alkoxycarbonyl] and methoxycarbonyl [$CH_3OC(=O)$—, a $C_2$alkoxycarbonyl].

"Alkyl" refers to a branched or unbranched hydrocarbon fragment containing the specified number of carbon atoms and having-one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Cinnamide" refers to a group of the

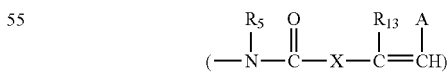

which includes both the 'conventional cinnamide' group when X is a direct bond and the 'unconventional cinnamide' group when X is C($R_{14}$,$R_6$)—Y—.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in *Handbook of Chemistry and Physics,* 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—CH$_2$OH, a C$_1$hydroxyalkyl) and 1-hydroxyethyl (—CHOHCH$_3$, a C$_2$hydroxyalkyl).

"Thioalkyl" refers to a sulfur atom substituted by an alkyl group, for example thiomethyl (CH$_3$S—, a C$_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be deactivated or blocked, so that fewer or no ions, respectively, are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of formula (I)" encompass compositions that contain more than one compound of formula (I).

Compounds of the Present Invention

The compounds of the present invention are amines which may be represented by formula (I):

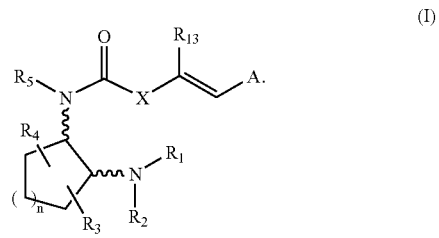

Compounds of formula (I) are aminocycloalkyl cinnamides. More specifically, these aminocycloalkyl cinnamides are substituted at position 2 of a cycloalkyl ring with an amine group —NR$_1$R$_2$. The cycloalkyl ring may also be substituted with additional substituents (designated as R$_3$ and R$_4$) as described in more detail below. In formula (I), n is selected from 1, 2, 3 and 4, and represents a number of carbon atoms such that when n equals 1, the ring shown in Formula (I) is a substituted cyclopentane (i.e., a cyclopentyl group), when n equals 2, the ring shown in Formula (I) is a cyclohexane (i.e., a cyclohexyl group), when n equals 3, the ring shown in Formula (1) is a substituted cycloheptane (i.e., a cycloheptyl group), and when n equals 4, the ring shown in Formula (I) is a substituted cyclooctane (i.e., a cyclooctyl group). Examples of specific embodiments of compounds represented by formula (I) are described below Depending upon the selection of substituents R$_1$ $_{and\ R2}$, The compounds of formula (I) may be primary, secondary, or tertiary amines (i.e., both R$_1$ and R$_2$ are hydrogen, only one of R$_1$ and R$_2$ is hydrogen, or neither of R$_1$ and R$_2$ are hydrogen, respectively). Where the amine is tertiary, it may be a cyclic amine. Amine substituents R$_1$ and R$_2$ may be independently selected from substituents which include hydrogen, alkyl groups containing from one to eight carbon atoms (i.e., C$_1$–C$_8$alkyl), alkoxyalkyl groups containing from three to eight carbon atoms (i.e., C$_3$–C$_8$alkoxyalkyl), alkyl groups containing from one to eight carbon atoms where one of the carbon atoms is substituted with a hydroxyl group (i.e., C$_1$–C$_8$hydroxyalkyl), and aralkyl groups containing from seven to twelve carbon atoms (i.e., C$_7$–C$_{12}$aralkyl).

Alternatively, R$_1$ and R$_2$, when taken together with the nitrogen atom to which they are directly attached in formula (I), may form a ring denoted by formula (II):

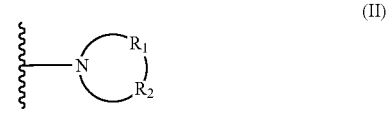

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, C$_1$–C$_3$hydroxyalkyl, oxo, C$_2$–C$_4$acyl, C$_1$–C$_3$alkyl, C$_2$–C$_4$alkylcarboxy, C$_1$–C$_3$alkoxy, C$_1$–C$_{20}$alkanoyloxy, or may be substituted to form a spiro five- or six-membered heterocyclic ring containing one or two heteroatoms selected from oxygen and sulfur (e.g., an acetal, thioacetal, ketal, or thioketal group); and any two adjacent additional carbon ring atoms may be fused to a $C_3$–$C_8$carbocyclic ring, and any one or more of the additional nitrogen ring atoms may be substituted with substituents selected from hydrogen, $C_1$–$C_6$alkyl, $C_2$–$C_4$acyl, $C_2$–$C_4$hydroxyalkyl and $C_3$–$C_8$alkoxyalkyl. Examples of substituents containing a fused ring system include the perhydroindolyl and 1,2,3,4-tetrahydroisoquinolinyl groups.

In connection with the ring of formula (II), any two adjacent ring atoms may be joined together by single or double bonds. Thus, the ring of formula (II) may be saturated or unsaturated, and an unsaturated ring may contain one, or more than one, sites of unsaturation. In other words, the ring of formula (II) may contain one or more double bonds, it being understood, however, that the unsaturated ring of formula (II) is chemically stable.

Alternatively, $R_1$ and $R_2$, when taken together with the 2-amino nitrogen of formula (I), may complete a bicyclic ring. Bicyclic rings include, for example, 3-azabicyclo [3.2.2]nonane, 2-azabicyclo[2.2.2]octane, 3-azabicyclo [3.1.0]hexane, and 3-azabicyclo[3.2.0]heptane. For these derivatives, the 2-substituents of the cycloalkyl cinnamides of formula (I) are the following groups: 3-azabicyclo[3.2.2] nonan-3-yl, 2-azabicyclo[2.2.2]octan-2-yl, 3-azabicyclo [3.1.0]hexan-3-yl, and 3-azabicyclo[3.2.0]heptan-3-yl.

Preferably for formula (II), $R_1$ and $R_2$, when taken together, contain only a single heteroatom. Preferred heteroatoms include nitrogen, oxygen and sulfur. An example of a ring in which $R_1$ and $R_2$ together include an oxygen heteroatom is the morpholinyl group. An example of a ring where $R_1$ and $R_2$ together include a second nitrogen heteroatom is the piperazinyl group.

Cycloalkyl substituents $R_3$ and $R_4$ may be independently attached to any of the ring positions except positions 1 and 2 (e.g., both $R_3$ and $R_4$ may be attached to the same ring position or each attached to different ring positions). $R_3$ and $R_4$ are independently selected from hydrogen, hydroxy, $C_1$–$C_6$alkyl, and $C_1$–$C_6$alkoxy, and, when both $R_3$ and $R_4$ are attached to the same cycloalkyl ring atom, may together form a spiro five- or six-membered heterocyclic ring containing one or two heteroatoms selected from oxygen and sulfur. Preferred heterocyclic substituents contain either a single oxygen or a single sulfur ring atom.

Depending upon the identity of X, the cinnamide side chain,

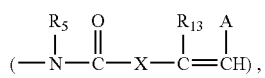

in formula (I) may take several forms. For example, a compound of formula (I) may have X as a —$C(R_6,R_{14})$—Y— group, where Y may be any of a direct bond, an oxygen atom (O), a sulfur atom (S) or a $C_1$–$C_4$alkylene group. $R_6$ and $R_{14}$ are independently selected from hydrogen, $C_1$–$C_6$alkyl, aryl and benzyl, or $R_6$ and $R_{14}$, when taken together with the carbon to which they are attached, may form a spiro $C_3$–$C_5$cycloalkyl. Thus, compounds of the invention include compounds of formula (I) where $R_6$ and $R_{14}$ are hydrogen and Y is a direct bond, such that X may be $CH_2$.

Alternatively, X may be a direct bond. Independent of the selections for A, X and other variables, $R_5$ is selected from hydrogen, $C_1$–$C_6$alkyl, aryl and benzyl.

Cinnamide side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$–$C_{12}$alkyl and $C_3$–$C_{13}$carbocyclic rings. Particularly preferred cyclic hydrocarbons include selected aromatic groups such as phenyl, 1-naphthyl, 2-naphthyl, indenyl, acenaphthyl, and fluorenyl and are represented by formulae (III), (IV), (V), (VI), (VII), or (VIII) respectively.

A suitable "A" group within the compounds of the present invention is a phenyl ring represented by formula (III):

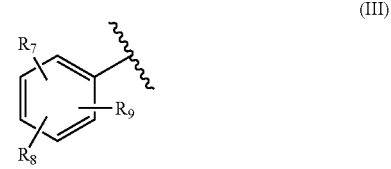

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl.

For compounds of formula (I) where X is a direct bond or $CH_2$, at least one of $R_7$, $R_8$ and $R_9$ is preferably selected from amine (—$NR_{15}R_{16}$, where $R_{15}$ and $R_{16}$ are independently hydrogen, acetyl, methanesulfonyl, and $C_1$–$C_6$alkyl), bromine, chlorine, fluorine, carboxy, hydrogen, hydroxy, hydroxymethyl, nitro, trifluoromethyl, $C_2$–$C_7$alkanoyloxy, $C_1$–$C_6$alkyl, $C_1$–$C_6$alkoxy, $C_2$–$C_7$alkylcarbonyl, $C_1$–$C_6$thioalkyl or aryl groups.

Other suitable "A" groups in compounds of the present invention are 1-naphthyl groups as represented by formula (IV):

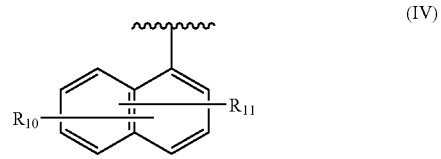

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl.

Other suitable "A" groups in compounds of the present invention are 2-naphthyl group as represented by formula (V):

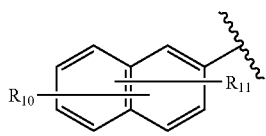
(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl, as defined above.

Other suitable "A" groups in compounds of the present invention are aromatic groups represented by formula (VI):

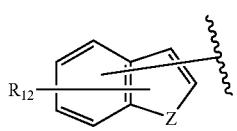
(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl. $C_1$–$C_6$thioalkyl, and $N(R_{15},R_{16})$ where $R_{15}$ and $R_{16}$ are independently selected from hydrogen, acetyl, methanesulfonyl, and $C_1$–$C_6$alkyl; and Z is selected from CH, $CH_2$, O, N and S, where Z may be directly bonded to the carbon atom in formula (I) that is shown directly bonded to "A" when Z is CH or N, or Z may be directly bonded to $R_{17}$ when Z is N, and $R_{17}$ is selected from hydrogen, $C_1$–$C_6$alkyl, $C_3$–$C_8$cycloalkyl, aryl and benzyl.

The aryl groups of formula (VI) are derivatives of indene, indole, benzofuran, and thianaphthene when Z is methylene, nitrogen, oxygen, and sulfur, respectively. Preferred heterocyclic groups of formula (VI) include indole where Z is NH, benzofuran where Z is 0, and thianaphthene where Z is S.

Another suitable "A" group in compounds of the present invention are acenaphthyl groups as represented by formula (VII):

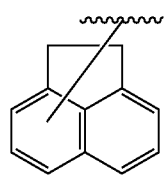
(VII)

Still another suitable "A" group in compounds of the present invention is the fluorenyl group represented by formula (VIII):

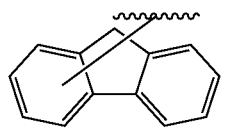
(VIII)

Preferably, cinnamide side chain component A is an acenaphthyl or fluorenyl group only when X is a direct bond or $CH_2$. In further preferred embodiments, the acenaphthyl group is a 1-acenaphthyl group, and the fluorenyl group is a 9-fluorenyl group.

As mentioned above, the present invention provides aminocycloalkyl cinnamides represented by formula (I). In a preferred embodiment X is $(CH_2)$—Y. For these embodiments, Y is preferably a direct bond, an oxygen atom, or a sulfur atom. In a particularly preferred embodiment, Y is a direct bond or an oxygen atom. In another preferred embodiment Y is a direct bond and X is $C(R_6,R_{14})$, where $R_6$ and $R_{14}$ are as defined above.

The following are further preferred compounds of the present invention:

(1R,2R)/(1S,2S)-N-Methyl-N-[2-(1-pyrrolidinyl)cyclohexyl] 3,4-dichlorocinnamide monohydrochloride

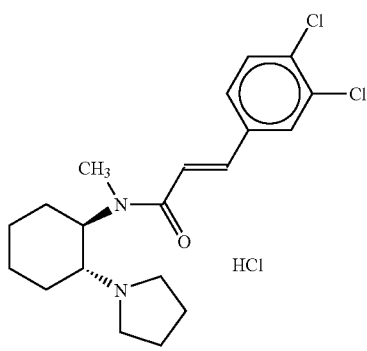

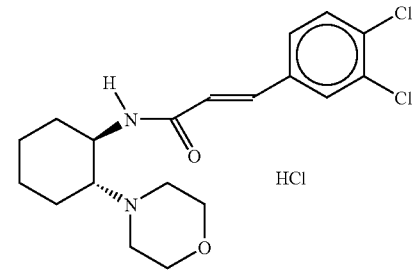

(1R, 2R)/(1S, 2S)-N-[2-(4-Morpholinyl)cyclohexyl] 3,4-dichlorocinnamide monohydrochloride -continued

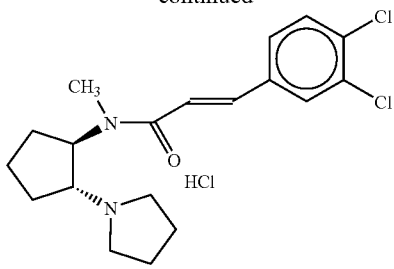

(1R, 2R)/(1S, 2S)-N-Methyl-N-[2-(1-pyrrolidinyl)cyclopentyl] 3,4-dichlorocinamide monohydrochloride Outline of Method of Preparation of Compounds of the Invention The aminocycloalkyl cinnamide compounds of the present invention contain amino and cinnamide sidechains disposed in a 1,2 arrangement on a cycloalkyl ring. Accordingly, the amino and cinnamide sidechains may be disposed in either a cis or trans relationship, relative to one another and the plane of the cycloalkyl ring. The present invention provides synthetic methodology whereby cis or trans compounds may be prepared.

The compounds of formula (I) may be synthesized in analogy with known methods, including those described in the following publications: B. R. de Costa et al., *J. Med. Chem.* 1989, 32, 1996; B. R. de Costa et al., *J. Med. Chem.* 1990, 33, 3100; and U.S. Pat. Nos. 4,579,863; 4,598,087; 4,656,182; 4,663,343; 4,737,493; 4,855,316; 5,130,309, and 5,506,257.

Cinnamic acids may be prepared by known methods (see, e.g., J. R. Johnson in *Organic Reactions*; R. Adams Editor; 1942, Vol. 1, p. 218; John Wiley and Sons, Inc. New York).

The individual enantiomers may be obtained from mixtures of the different forms by known methods of resolution, such as the isolation or formation of the diastereomers, followed by recrystallization. Alternatively, the pure enantiomeric forms can be obtained by preparative chiral High Performance Liquid Chromatography (HPLC).

The synthetic procedures described herein, especially when taken with the general knowledge in the art, provide sufficient guidance to those of ordinary skill in the art to perform the synthesis, isolation, and purification of the compounds of the present invention.

Compositions and Modes of Administration

In another embodiment, the present invention provides compositions which include a cycloalkylamine compound as described above in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing a cycloalkylamine compound as described above, in admixture with a pharmaceutically acceptable carrier, excipient or diluent. The invention further provides a pharmaceutical composition containing an effective amount of a cycloalkylamine compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of cycloalkylamine compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. For instance, epinephrine may be combined with an aminocycloalkyl cinnamide compound of the invention, to provide a composition useful to induce local anesthesia. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a cycloalkylamine compound as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof, excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydoxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active cycloalkylamine compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cycloalkylamine compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the cycloalkylamine compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment of arrhythmia, diseases of the central nervous system, convulsions, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, hypotension, Alzheimer's disease and other mental disorders, and alopecia. Other agents known to cause libido enhancement, local analgesia or anesthesia may be combined with compounds of the present invention.

The pharmaceutical compositions may be prepared by methodology well known in the pharmaceutical art. The aminocycloalkyl compounds of the invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the cycloalkylamine compound with water, and preferably buffering agents, so as to form a solution. The water is preferably sterile pyrogen-free water. A surfactant may be added to facilitate the formation of a homogeneous solution or suspension. Surfactants are compounds that non-covalently interact with the cycloalkylamine compound so as to facilitate dissolution or homogeneous suspension of the cycloalkylamine compound in the aqueous delivery system. Surfactants are desirably present in aqueous compositions of the invention because the cycloalkylamine compounds of the present invention are typically hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

Pharmacological Testing

As noted above, the present invention provides for utilizing the compounds described above in in vitro and in vivo methods. In one embodiment, ion channels, such as cardiac sodium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating or preventing a variety of diseases or disorders caused by defective or inadequate function of the ion channels. The compounds of the invention are found to have significant activity in modulating ion channel activity both in vivo and in vitro.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. The diseases and conditions to which the compounds, compositions and methods of the present invention may be applied as follows: arrhythmia, diseases of the central nervous system, convulsion, epileptic spasms, depression, anxiety, schizophrenia, Parkinson's disease, respiratory disorders, cystic fibrosis, asthma, cough, inflammation, arthritis, allergies, gastrointestinal disorders, urinary incontinence, irritable bowel syndrome, cardiovascular diseases, cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease or other mental disorder, and alopecia.

Furthermore, the present invention provides a method for producing local analgesia or anesthesia in a warm-blooded animal which includes administering to a warm-blooded animal in need thereof an effective amount of a compound of formula (I) or a pharmaceutical composition containing a compound of formula (I). These methods may be used to relieve or forestall the sensation of pain in a warm-blooded animal.

Furthermore, the present invention provides a method wherein a preparation that contains ion channels is exposed to, or a warm-blooded animal (e.g., a mammal, such as a human) is administered an effective amount of an aminocycloalkyl cinnamide compound of the invention. Suitable preparations containing cardiac sodium channels include cells isolated from cardiac tissue as well as cultured cell lines. The step of contacting includes, for example, incubation of ion channels with a compound under conditions and for a time sufficient to permit modulation of the activity of the channels by the compound.

In another embodiment, the compounds described above are provided for treating arrhythmia. As used herein, "treating arrhythmia" refers to both therapy for arrhythmia and for the prevention of arrhythmias occurring in a heart that is susceptible to arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred. The dosage amount and frequency are selected to attain effective levels of the agent without harmful effects. It will generally range from a dosage of from about 0.1 to about 100 mg/kg/day, and typically from about 0.1 to 10 mg/kg where administered orally or intravenously for antiarrhythmic effect.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocycloalkyl cinnamide compound of the invention may be co-administered with epinephrine in order to include local anesthesia.

In order to assess whether a compound of the present invention has a desired pharmacological activity, it is subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous boluses every 8 minutes to a pentobarbital anesthetized rat. The effects of the compound on blood pressure, heart rate and the ECG are measured at 30 seconds, 1, 2, 4 and 8 minutes after each dose. Increasing doses are given until the animal dies. The cause of death is identified as being of either respiratory or cardiac origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions, and preferably on all these parameters.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the atrial and ventricular epicardium. After the pericardium is removed from the heart a recording/stimulation electrode is sewn onto the epicardial surface of the atria and ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system are assessed.

The effects of a compound on the ECG and responses to electrical stimulation are also assessed in intact, anesthetized monkeys (*Macaca fascilaris*). In this preparation, a blood pressure cannula and ECG electrodes are suitably placed in an anesthetized baboon. In addition, a stimulating electrode is placed onto the atria and ventricle, together with monophasic action potential electrodes. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle applied to the shaved back of a guinea pig (*Cavia porcellus*) is assessed following subcutaneous administration of (e.g. 50 μl, 10 mg/ml) a solution of the compound in saline to raise a visible bleb on the skin. Each test is performed on the central area of the bleb and also on its periphery to ascertain the diffusion of the test solution from the point of administration. If the test animal produces a flinch in response to the stimulus, this demonstrates the absence of blockade of pain sensation. Testing is performed at intervals for up to 4 hours post administration. The sites of bleb formation are examined after 24 hours to determine if skin abnormalities arise from the local administration of test substances or the vehicle (e.g. saline) used in the preparation of the test solutions.

Other Compositions

The present invention also provides kits that contain a pharmaceutical composition which includes one or more compounds of the above formulae. The kit also includes instructions for the use of the pharmaceutical composition for modulating the activity of ion channels, for the treatment of arrhythmia or for the production of local analgesia and/or anesthesia, and for the other utilities disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" both refers to diethyl ether; "h." refers to hours; "min." refers to minutes; "GC" refers to gas chromatography; "v/v" refers to volume per volume; and ratios are weight ratios unless otherwise indicated.

EXAMPLES

Example 1

Preparation of Compound 1

(1R,2R)/(1S,2S)-N-Methyl-N-[2-(1-pyrrolidinyl)cyclohexyl] 3,4-dichlorocinnamide monohydrochloride The synthetic sequence of this Example is shown in FIG. 1A.

Acid chloride formation: 3,4-dichlorocinnamic acid (5 g, 23 mmol, Aldrich cat. #14,470-3) was refluxed in thionyl chloride (12 mL, BDH cat. #30417) under nitrogen for 1 h. At first the white solid did not dissolve, but became pinkish. After refluxing the solution became clear and almost colorless. After the mixture was stirred at room temperature for a further 1 h, the thionyl chloride was removed in vacuo (using 3×5 mL $CCl_4$). The product was then dissolved in dichloromethane (10 mL).

Amide formation: the above acid chloride solution was added via cannula to a cooled solution of the racemic diamine, (1R,2R)/(1S,2S)-N-Methyl-N-[2-(1-pyrrolidinyl)cyclohexyl]-amine (prepared according to U.S. Pat. No. 4,579,863 and *J. Med. Chem.*, 1982, 25, 1125) (4 g, 22 mmol) in dichloromethane (10 mL) under nitrogen. The mixture was stirred at 0° C. for 10 min., and then at room temperature for 1 h. Ether (15 mL) was added and a thick white precipitate formed. The crude hygroscopic product (9.7 g) was filtered off and washed with ether (2×10 mL). It was recrystallized from hot ethyl acetate-methanol, to give 2 crops of white crystalline solid (7.5 g), which were dried by heating in vacuo to 60° C. for 3 h. A third crop of cream colored solid was also obtained (0.9 g). The flocculent precipitate was filtered off and washed with ether and dried in vacuo. NMR indicated that the combined first two crops contained ethyl acetate, so they were recrystallized from hot methanol (7 mL) -ether, to give 1st crop (5.3 g); 2nd crop (0.85 g). Dried in vacuo at 60° C. for 4 h. Yield of pure product (67%).

IR, and $^3$C-NMR spectra were recorded for solutions in $CDCl_3$.

Microanalysis: C, 55.60; H, 6.54; N, 6.41% (theoretical for $C_{20}H_{27}N_2OCl_3$: C 57.50, H 6.51, N 6.70%).

Example 2

Preparation of Compound 2

Figure 1B:
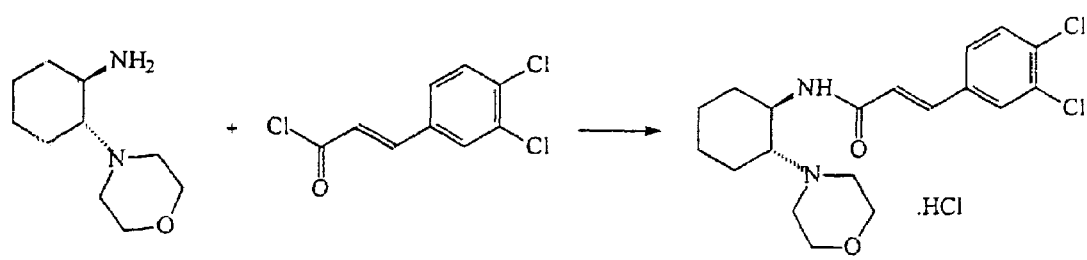

(1R,2R)/(1S,2S)-N-[2-(4-Morpholinyl)cyclohexyl] 3,4-dichlorocinnamide monohydrochloride The synthetic sequence of this Example is shown in FIG. 1B.

Acid chloride formation: To 3,4-dichlorocinnamic acid (2.17 g, 10 mmol, Aldrich Cat. # 14,470-3) under nitrogen was added thionyl chloride (10 mL, Aldrich Cat. # 32,054-4). The reaction mixture was refluxed for 1 hour and then 30 min. at room temperature. The excess of thionyl chloride was removed in vacuo to leave a greenish solid which was dissolved in dichloromethane (10 mL).

NH Amide formation: To the chilled (0° C.) solution of (1R,2R)/(1S,2S)-[2-(4-morpholinyl)cyclohexyl]amine (1.75 g, 9.5 mmol) in dichloromethane was added via cannula the above acid chloride solution. Upon completion of the addition the reaction mixture was allowed to warm up to room temperature and was stirred overnight. GC analysis showed that the reaction was completed. The solvent was evaporated in vacuo, the residue taken up with ether and triturated, evaporation in vacuo of the solvent afforded a pink solid. The crude salt was partitioned between 1N aqueous NaOH (50 mL) and dichloromethane (50 mL). The organic layer was collected and dried over sodium sulfate. Evaporation in vacuo of the solvent afforded an oil which was dissolved in ether (50 mL) and treated with a HCl saturated solution of ether (50 mL). The resultant precipitate was collected and rinsed with ether (2×50 mL). Recrystallization in ethanol yielded 1.86 g of the desired product.

Microanalysis: C, 54.31; H, 6.89; N, 5.90% (theoretical for $C_{19}H_{25}N_2O_2Cl_3$.1.0$C_2H_5OH$ C, 54.14; H, 6.71; N, 6.01%

Example 3

Preparation of Compound 3

Figure 1C:
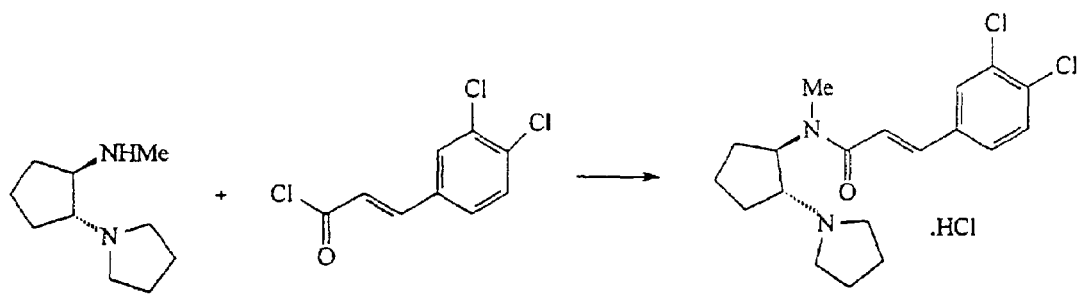

(1R,2R)/(1S,2S)-N-Methyl-N-[2-(1-pyrrolidinyl)cyclopentyl]3,4-dichlorocinnamide monohydrochloride The synthetic sequence of this Example is shown in FIG. 1C.

Acid chloride formation: 3,4-dichlorocinnamic acid (2.71 g, 12.5 mmol, Aldrich cat. #14,470-3) was refluxed in thionyl chloride (10 mL, Aldrich cat. #32,054-4) under nitrogen for 2 h. After the reaction mixture was stirred at room temperature for a further 1 h., the thionyl chloride was removed in vacuo (using 3×5 mL $CCl_4$) to give an off-white solid, which was dissolved in dichloromethane (8 mL).

Amide formation: the acid chloride solution was added via cannula to a room temperature solution of (1R,2R)/(1S,2S)-N-methyl-N-[2-(1-pyrrolidinyl)cyclopentyl]-amine (2.0 g, 11.9 mmol) in dichloromethane (8 mL) under nitrogen. The reaction was stirred at room temperature for 1 h. Ether (30 mL) was slowly added to the reaction mixture, causing the formation of an orange/brown oil. The solvent was removed in vacuo and the residue was dissolved in 1N aq. HCl (100 mL). The aqueous layer was washed with ether (1×60 mL. 2×30 mL), and then was basified (pH 12) by the addition of 50% aq. NaOH solution. A yellow oil was formed, and the aqueous/oil mixture was extracted with dichloromethane (1×60 mL, 2×40 mL). The combined dichloromethane extracts were dried over sodium sulphate and the solvent was removed in vacuo. The residue (4.3 g) was purified by column chromatography (silica gel, methanol eluant). The isolated product was dissolved in 1N aq. HCl (60 mL), and NaCl (12 g) was added to the resultant solution, which was then extracted with chloroform (3×60 mL). The chloroform extracts were combined and dried over sodium sulphate. The solvent was removed in vacuo. The crude HCl salt (5.35 g) was recrystallized from hot hexane (25 mL)/hot acetone (40 mL). The solution was slowly cooled to room temperature and left at ~5° C. for two days. Two crops of recrystallized product were collected, rinsed with ether, and dried in vacuo. Wt. of 1st crop: 3:91 g, 2nd crop: 0.14 g. The former was used for compound characterization.

IR, and $^{13}$C-NMR spectra were recorded for solutions in CDCl$_3$. The NMR indicated the presence of two isomers (1:1).

Microanalysis: C, 56.46; H, 6.15; N, 6.79% (theoretical for C$_{19}$H$_{25}$N$_2$OCl$_3$; C, 56.52; H, 6.24; N, 6.94%).

Example 4

Assessment of Antiarrhythmic Efficacy

Antiarrhythmic efficacy was assessed by investigating the effect of a compound on the incidence of cardiac arrhythmias in conscious rats subjected to coronary artery occlusion. Rats weighing 200–300 gms were subjected to preparative surgery and assigned to groups in a random block design. In each case, the animal was anesthetized with halothane during surgical preparation. The left femoral artery was cannulated for measurement of mean arterial blood pressure and withdrawal of blood samples. The left femoral vein was also cannulated for injection of drugs. The thoracic cavity was opened and a polyethylene occluder loosely placed around the left anterior descending coronary artery. The thoracic cavity was then closed. ECG was recorded by insertion of electrodes placed along the anatomical axis of the heart. All cannulae and electrode leads were exteriorized in the mid scapular region. In a random and double-blind manner, about 0.5 to 2 hours post-surgery, an infusion of vehicle, or the compound to be tested was given. After 5 to 15 minutes infusion, the occluder was pulled so as to produce coronary artery occlusion. ECG, arrhythmias, blood pressure, heart rate and mortality were monitored for 30 minutes after occlusion. Arrhythmias were recorded as ventricular tachycardia (VT) and ventricular fibrillation (VF) and scored according to Curtis, M. J. and Walker, M. J. A., *Cardiovasc. Res.* 22:656 (1988) (see Table 1).

TABLE 1

| Score | Description |
| --- | --- |
| 0 | 0–49 VPBs |
| 1 | 50–499 VPBs |
| 2 | >499 VPBs and/or 1 episode of spontaneously reverting VT or VF |
| 3 | >1 episode of VT or VF or both (>60s total combined duration) |
| 4 | VT or VF or both (60–119s total combined duration) |
| 5 | VT or VF or both (>119s total combined duration) |
| 6 | fatal VF starting at >15 min after occlusion |
| 7 | fatal VF starting at between 4 min and 14 min 59s after occlusion |
| 8 | fatal VF starting at between 1 min and 3 min 59s after occlusion |
| 9 | fatal VF starting <1 min after occlusion |

Where:
VPB = ventricular premature beats
VT = ventricular tachycardia
VF = ventricular fibrillation Rats were excluded from the study if they did not exhibit pre-occlusion serum potassium concentrations within the range of 2.9–3.9 mM. Occlusion is associated with increases in R-wave height and "S-T" segment elevation; and an occluded zone (measured after death by cardiogreen dye perfusion) in the range of 25%–50% of total left-ventricular weight.

Table 2 describes the result of tests of the compounds described therein as values of a given infusion rate in micromol/kg/min. (ED$_{50}$AA) which will reduce the arrhythmia score in treated animals to 50% of that shown by animals treated only with the vehicle in which the test drug(s) is dissolved.

TABLE 2

| Compound | ED$_{50}$AA |
| --- | --- |
| #1 | 0.4 |
| #2 | ND |
| #3 | 2 |

ND = Not Determined

Example 5

Measurement of ECG Parameters

Rats weighing 200–250 gms were used in this example. Animals were anesthetized with 60 mg/kg pentobarbital i.p. The carotid artery and jugular vein were cannulated for measurement of blood pressure and drug injection, respectively. ECG was recorded by insertion of electrodes placed along the anatomical axis of the heart. All compounds were given as bolus injections.

Various ECG parameters were measured. Table 3 describes the results of the tests as ED$_{25}$ (micromol/kg) which are the doses required to produce a 25% increase in the parameter measured (ne=not estimated). The increases in P-R interval and QRS interval indicate cardiac sodium channel blockage while the increase in Q-T interval indicates ancillary cardiac potassium channel blockage which is the property of a type 1a antiarrhythmic.

TABLE 3

| Compound | PR | QRS | QT |
| --- | --- | --- | --- |
| #1 | 2.8 | ND | 8 |
| #2 | 60 | 64 | 9 |
| #3 | 8 | 12 | 5 |

ND = Not Determined

Example 6

Assessment of Sodium Channel Blockage

Rats were prepared according to the preceding procedure. Two silver stimulating electrodes were inserted through the chest wall and implanted in the left ventricle. Square wave stimulation was used to determine threshold current for capture, ventricular fibrillation threshold current, and effective refractory period (Howard, P. G. and Walker, M. J. A., *Proc. West. Pharmacol. Soc.* 33:123–127 (1990)). Table 4 contains ED$_{25}$ values for these indices of cardiac sodium channel blockage, where the ED$_{25}$ is the infusion rate in micromol/kg/minute of compound required to elicit a 25% increase from control. The increases in refractoriness indicate ancillary blockage of potassium channels. The threshold current for capture is represented by "It". The fibrillation threshold current is represented by "VFT". The effective refracting period is represented by "ERP".

TABLE 4

| Compound | It | VFT | ERP |
| --- | --- | --- | --- |
| #1 | 0.8 | 0.7 | 1.4 |
| #2 | 12 | 3 | 4 |
| #3 | 4 | 12 | 2 |

Example 7

Canine Vagal-AF Model

General Methods

Mongrel dogs of either sex weighing 1549 kg were anesthetized with morphine (2 mg/kg im initially, followed by 0.5 mg/kg IV every 2 h) and α-chloralose (120 mg/kg IV followed by an infusion of 29.25 mg/kg/h; St.-Georges et al., 1997). Dogs were ventilated mechanically with room air supplemented with oxygen via an endotracheal tube at 20 to 25 breaths/minute with a tidal volume obtained from a nomogram. Arterial blood gases were measured and kept in the physiological range ($SAO_2$>90%, pH 7.30–7.45). Catheters were inserted into the femoral artery for blood pressure recording and blood gas measurement, and into both femoral veins for drug administration and venous sampling. Catheters were kept patent with heparinized 0.9% saline solution. Body temperature was maintained at 37–40° C. with a heating blanket.

The heart was exposed via a medial thoracotomy and a pericardial cradle was created. Three bipolar stainless steel, Teflon™-coated electrodes were inserted into the right atria for recording and stimulation, and one was inserted into the left atrial appendage for recording. A programmable stimulator (Digital Cardiovascular Instruments, Berkeley, Calif.) was used to stimulate the right atrium with 2 ms, twice diastolic threshold pulses. Two stainless steel, Teflon™-coated electrodes were inserted into the left ventricle, one for recording and the other for stimulation. A ventricular demand pacemaker (GBM 5880, Medtronics, Minneapolis, Minn.) was used to stimulate the ventricles at 90 beats/minute when (particular during vagal-AF) the ventricular rate became excessively slow. A P23 ID transducer, electrophysiological amplifier (Bloom Associates, Flying Hills, Pa.) and paper recorder (Astromed MT-95000, Toronto, ON, Canada) were used to record ECG leads II and III, atrial and ventricular electrograms, blood pressure and stimulation artefacts. The vagi were isolated in the neck, doubly-ligated and divided, and electrodes inserted in each nerve (see below). To block changes in β-adrenergic effects on the heart, nadolol was administered as an initial dose of 0.5 mg/kg iv, followed by 0.25 mg/kg IV every two hours.

Atrial Fibrillation Model

Drug effects to terminate sustained AF maintained during continuous vagal nerve stimulation were assessed. Unipolar hook electrodes (stainless steel insulated with Teflon™, coated except for the distal 1–2 cm) were inserted via a 21 gauge needle within and parallel to the shaft of each nerve. In most experiments, unipolar stimuli were applied with a stimulator (model DS-9F, Grass Instruments, Quincy, Mass.) set to deliver 0.1 ms square-wave pulses at 10 Hz and a voltage 60% of that required to produce asystole. In some experiments, bipolar stimulation was used. The voltage required to produce asystole ranged between 3–20 volts. Under control conditions, a short burst of rapid atrial pacing (10 Hz, four times diastolic threshold) was delivered to induce AF which was ordinarily sustained for more than 20 minutes. The vagal stimulation voltage was adjusted under control conditions, and then readjusted after each treatment to maintain the same bradycardic effect. AF was defined as rapid (>500 minute under control conditions), irregular atrial rhythm with varying electrogram morphology.

Measurement of Electrophysiological Variables and Vagal Response

Diastolic threshold current was determined at a basic cycle length of 300 ms by increasing the current 0.1 mA incrementally until stable capture was obtained. For subsequent protocols current was set to twice diastolic threshold. Atrial and ventricular ERP was measured with the extra-stimulus method, over a range of S1S2 intervals at a basic cycle length of 300 ms. A premature extrastimulus S2 was introduced every 15 basic stimuli. The S1 S2 interval was increased in 5 ms increments until capture occurred, with the longest S1S2 interval consistently failing to produce a propagated response defining ERP. Diastolic threshold and ERP were determined in duplicate and averaged to give a single value. These values were generally within 5 ms. The interval between the stimulus artefact and the peak of the local electrogram was measured as an index of conduction velocity. AF cycle length (AFCL) was measured during vagal-AF by counting the number of cycles (number of beats −1) over a 2-second interval at each of the atrial recording sites. The three AFCLs measurements were averaged to obtain an overall mean AFCL for each experimental condition.

The stimulus voltage-heart rate relationship for vagal nerve stimulation was determined under control conditions in most experiments. The vagal nerves were stimulated as described above with various voltages to determine the voltage which caused asystole (defined as a sinus pause greater than 3 seconds). The response to vagal nerve stimulation was confirmed under each experimental condition and the voltage adjusted to maintain the heart rate response to vagal nerve stimulation constant. In cases in which is was not possible to produce asystole, vagal nerve stimulation was adjusted to a voltage which allowed two 20-minute episodes of vagal-AF to be maintained under control conditions (see below).

Experimental Protocols

Some of the experimental groups studied are summarized in Table 5. Each dog received only one drug at doses indicated in Table 5. The first series of experiments were dose ranging studies, followed by blinded study in which 1–3 doses were given. All drugs were administered IV via an infusion pump, with drug solutions prepared freshly in plastic containers on the day of the experiment. Vagal stimulation parameters were defined under control conditions as described above, and maintenance of AF during 20 minutes of vagal nerve stimulation under control conditions was verified. After the termination of AF, the diastolic threshold and ERP of the atrium and ventricle were determined. Subsequently, these variables were reassessed in the atrium under vagal nerve stimulation. Electrophysiological testing usually took 15–20 minutes. The heart rate response to vagal nerve stimulation was confirmed and the vagal-AF/electrophysiological testing protocol was repeated. A pre-drug blood sample was obtained and vagal-AF reinstituted. Five minutes later, one of the treatments was administered at doses shown in Table 5. The total dose was infused over 5 minutes and a blood sample obtained immediately thereafter. No maintenance infusion was given. If AF terminated within 15 minutes, the electrophysiological measurements obtained under control conditions were repeated and a blood sample was obtained. If AF was not terminated by the first dose (within 15 minutes), a blood sample was obtained and vagal stimulation was discontinued to allow a return to sinus rhythm. The electrophysiological measurements were repeated and a third and final blood sample for this dose was obtained. AF was reinitiated and the vagal-AF/drug infusion/electrophysiological testing protocol was repeated until AF was terminated by the drug.

Statistical Analysis

Group data are expressed as the mean ±SEM. Statistical analysis was carried out for effective doses for AFCL, and ERP using a t-test with a Bonferroini correction for multiple comparisons. Drug effects on blood pressure, heart rate, diastolic threshold and ECG intervals were assessed at the median dose for termination of AF. Two tailed tests were used and a $p<0.05$ was taken to indicate statistical significance.

TABLE 5

EXPERIMENTAL GROUPS AND DOSES OF DRUGS

| Drug | Dose range tested (µmol/kg) | Effective doses for terminating AF (µmol/kg) | Mean dose required for termination of AF (µmol/kg) | Median dose required for termination of AF (µmol/kg) |
|---|---|---|---|---|
| Flecainide | 1.25–10 | 4–2.5; 1–10 | 4 ± 2 | 2.5 |
| Compound 1 | 0.25–20 | 1.5; 4–10; 1–20 | 11 ± 2 | 10 |

A single drug was administered to each dog over the dose range specified until AF was terminated. The number of dogs in which AF was terminated at each dose is shown (number of dogs-dose, in µmol/kg). The mean±SEM as well as the median dose required to terminate AF is shown. Each dog received only one drug.

Results

The two drugs (flecainide and Compound 1) did not reduce blood pressure or heart rate at the median dose for termination of vagal-AF. The heart rate response to vagal nerve stimulation was similar in all groups and was not influenced by any of the drugs tested. Vagal nerve stimulation at 60% of the voltage required to produce asystole (10±1 V) produced a 1.3±0.1 second pause. The two drugs tested were effective, but the efficacy for terminating AF was greater for Compound 1 (6/6 dogs; 100%) than for flecainide (5/6 dogs; 80%) (Table 5). The dose required to terminate AF depended on the drug considered (Table 5). AFCL was prolonged prior to AF termination in all cases. Drug effects on AFCL length were dose related and doses that were effective in terminating AF produced greater increases in AFCL than those that did not.

The conversion rates for the drugs tested in the vagal-AF model were comparable to those found for Class I drugs in this model (Wang et al., 1991, Wang J., Bourne G. W., Wang Z., Villemaire C., Talajic M., Nattel S., *Circulation*. 88(3): 1030–44, 1993) and those found clinically (see Nattel S., Hadjis T., Talajic M., *Drugs*. 48(3):345–71, 1994, or Steinbeck G., Remp T., Hoffmann E., *Journal of Cardiovascular Electrophysiology*. 9(8 Suppl):S104–8, 1998, for a review). Flecainide terminated AF in 5/6 dogs consistent with its published efficacy (Wang Z., Page P., Nattel S., *Circulation Research*. 71(2):271–87, 1992). The efficacy of Compound 1 was higher than that reported for low dose sotalol (2 mg/kg iv) but comparable to high dose sotalol (8 mg/kg iv; Wang J., Bourne G. W., Wang Z., Villemaire C., Talajic M., Nattel S., *Circulation*. 88(3):1030–44, 1993), ambasilide and azimilide (Nattel S., *Cardiovascular Research*. 37(3):567–77, 1998).

AFCL has been used as an index of atrial ERP during AF. All of the drugs tested in the present study prolonged AFCL during vagal nerve stimulation. Flecainide prolonged AFCL to a similar degree in the present study to that reported previously (Wang Z., Page P., Nattel S., *Circulation Research*. 71(2):271–87, 1992). The increases in AFCL produced by Compound 1 prior to termination of AF were similar to those seen with sotalol, dofetilide, azimilide, and ambasilide in previous studies (see Wang J., Feng J., Nattel S., *Circulation*. 90(4):2032–40, 1994; Nattel, S., *Cardiovascular Research*. 37(3):567–77, 1998). Drug-induced increases of 60–100 ms appear to be associated with AF termination in this model. In about 60% of the dogs studied, AF was induced during the determination of ERP in the presence of vagal nerve stimulation. No differences were noted between drugs for preventing initiation of AF in this setting. In dogs in which AF was induced under control conditions, flecainide prevented induction in 2/4 while Compound 1 prevented induction in 4/5. After completing the electrophysiological testing, it was possible to induce AF in all dogs with the exception of 2/6 dogs in the Compound 1 group. Note that reinduction attempts took place after a period of time sufficient to permit significant drug redistribution and lower plasma concentrations.

At effective doses, both drugs tested prolonged atrial ERP. In all cases, ERP was reduced during vagal nerve stimulation. Compound 1 also prolonged atrial ERP more during vagal nerve stimulation.

In summary, the results of this study demonstrate the effectiveness of Compound 1 for terminating AF in the canine vagal-AF model. The conversion rates are similar to those reported for a variety of other class I and III drugs in this model. The effectiveness of flecainide in the present study was comparable to that previously reported. All of the drug prolonged AFCL prior to termination of AF; effects which are globally consistent with the wave length of reentry model for termination of AF. The dosing regimen was not optimized.

Example 8

Canine Sterile Pericarditis Model

This model has been used to characterize the mechanisms of AF and atrial flutter (AFL). Waldo and colleagues have found that AF depends on reentry and that the site of termination is usually an area of slowed conduction. This canine model is prepared by dusting the exposed atria with talcum powder followed by "burst" pacing the atria over a period of days after recovery. AF is inducible two days after surgery, however, by the fourth day after surgical preparation; sustainable atrial flutter is the predominant inducible rhythm. The inducibility of AF at day 2 is somewhat variable, such that only 50% of dogs may have sustained AF (generally <60 minutes) for a requisite of 30 minutes. However, the sustainable atrial flutter that evolves by the fourth day is inducible in most preparations. Atrial flutter is more readily "mapped" for purposes of determining drug mechanisms. Inducibility of AF subsides after the fourth day post-surgery, similar to the AF that often develops following cardiac surgery that the sterile pericarditis model mimics. There may be an inflammatory component involved in the etiology of post-surgery AF that would provide a degree of selectivity to an ischaemia or acid selective drug. Similarly, while coronary artery bypass graft (CABG) surgery is performed to alleviate ventricular ischaemia, such patients may also be at risk for mild atrial ischaemia due to coronary artery disease (CAD). While atrial infarcts are rare, there has been an association between AV nodal artery stenosis and risk for AF following CABG surgery. Surgical disruption of the autonomic innervation of the atria may also play a role in AF following CABG.

Methods

Studies were carried out in a canine model of sterile percarditis to determine the potency and efficacy of Compound 1 in terminating atrial fibrillation/flutter. Atrial flutter or fibrillation was induced 2 to 4 days after creation of sterile pericarditis in adult mongrel dogs weighing 19 kg to 25 kg. In all instances, the atrial fibrillation or flutter lasted longer than 10 minutes. All studies were performed in accordance with guidelines specified by our Institutional Animal Care and Use Committee, the American Heart Association Policy on Research Animal Use, and the Public Health Service Policy on Use of Laboratory Animals.

Creation of the Sterile Pericarditis Atrial Fib/Flutter Model

The canine sterile pericarditis model was created as previously described. At the time of surgery, a pair of stainless steel wire electrodes coated with FEP polymer except for the tip (O Flexon, Davis and Geck) were sutured on the right atrial appendage, Bachman's bundle and the posteroinferior left atrium close to the proximal portion of the coronary sinus. The distance between each electrode of each pair was approximately 5 mm. These wire electrodes were brought out through the chest wall and exteriorized posteriorly in the interscapular region for subsequent use. At the completion of surgery, the dogs were given antibiotics and analgesics and then were allowed to recover. Postoperative care included administration of antibiotics and analgesics.

In all dogs, beginning on postoperative day 2, induction of stable atrial fibrillation/flutter was attempted in the conscious, non-sedated state to confirm the inducibility and the stability of atrial fib/flutter and to test the efficacy of the drugs. Atrial pacing was performed through the electrodes sutured during the initial surgery. On postoperative day 4, when stable atrial flutter was induced, the open-chest study was performed.

For the open-chest study, each dog was anesthetized with pentobarbital (30 mg/kg IV) and mechanically ventilated with 100% oxygen by use of a Boyle model 50 anesthesia machine (Harris-Lake, Inc.). The body temperature of each dog was kept within the normal physiological range throughout the study with a heating pad. With the dog anesthetized, but before the chest was opened, radiofrequency ablation of the His bundle was performed to create complete atrioventricular (AV) block by standard electrode catheter techniques. This was done to minimize the superimposition of atrial and ventricular complexes during subsequent recordings of unipolar atrial electrograms after induction of atrial flutter. After complete AV block was created, an effective ventricular rate was maintained by pacing of the ventricles at a rate of 60 to 80 beats per minute with a Medtronic 5375 Pulse Generator (Medtronic Inc.) to deliver stimuli via the electrodes sutured to the right ventricle during the initial surgery.

Determination of Stimulus Thresholds and Refractory Periods During Pacing

For the induction of AF/AFL, one of two previously described methods was used: (1) introduction of one or two premature atrial beats after a train of 8 paced atrial beats at a cycle length of 400 ms, 300 ms, 200 ms, or 150 ms, or (2) rapid atrial Pacing for Periods of 1 to 10 seconds at rates incrementally faster by 10 to 50 beats per minute than the spontaneous sinus rate until atrial flutter was induced or there was a loss of 1:1 atrial capture. Atrial pacing was performed from either the right atrial appendage electrodes or the posteroinferior left atrial electrodes. All pacing was performed using stimuli of twice threshold for each basic drive train with a modified Medtronic 5325 programmable, battery-powered stimulator with a pulse width of 1.8 ms.

After the induction of stable atrial fib/flutter (lasting longer than 10 minutes), the atrial fib/flutter cycle length was measured and the initial mapping and analysis were performed to determine the location of the atrial fib/flutter reentrant circuit. Atrial flutter was defined as a rapid atrial rhythm (rate, >240 beats per minute) characterized by a constant beat-to-beat cycle length, polarity, morphology, and amplitude of the recorded bipolar electrograms.

Drug Efficacy Testing Protocol

1. Effective refractory periods (ERPs) were measured from three sites: right atrial appendage (RAA), posterior left atrium (PLA), and Bachman's Bundle (BB), at two basic cycle lengths 200 and 400 ms.
2. Pace induce A-Fib or AFL. This was attempted for one hour. If no arrhythmia was induced, no further study was done on that day.
3. If induced, AF must have been sustained for 10 minutes. Then a waiting period was allowed for spontaneous termination or 20 minutes, whichever came first.
4. AF was then reinduced and 5 minutes was allowed before starting drug infusion.
5. Drug was then infused in a bolus over 5 minutes.
6. If AF terminated with the first dose then a blood sample was taken and ERP measurements were repeated.
7. Five minutes was allowed for the drug to terminate. If there was no termination then the second dose was given over 5 minutes.
8. After termination and ERPs were measured, a second attempt to reinduce AF was tried for a period of ten minutes.
9. If reinduced and sustained for 10 minutes, a blood sample was taken and the study repeated from #3 above.
10. If no reinduction, then the study was over.

Results

The effect of Compound 1 on 2 episodes of AFL and 3 episodes of AF were recorded, and one out of those three episodes of AF was reinduction after first dose. Both episodes of AFL terminated during administration of the first dose (10 µmol/kg; average actual amount delivered=3.5 µmol/kg), and also all three episodes of AF terminated during administration of the first dose (10 µmol/kg; average actual amount delivered=7 µmol/kg). None of these episodes of AFL could be reinduced. There was no significant change in thresholds and effective refractory periods (ERPs) before and after drug, determined by the paired t-test. No adverse effects were noted.

Compound 1 was effective in terminating episodes of atrial fibrillation/flutter in this model. A prolongation in atrial fib/flutter cycle length (AFCL) generally preceded termination of the arrhythmia. Limited effects on atrial refractory periods measured after arrhythmia termination may have been due to pharmacokinetic redistribution at the time of measurement. There was no proarrhythmia or cardiovascular adverse events seen during drug treatment.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound of formula (I), or a solvate or pharmaceutically acceptable salt thereof:

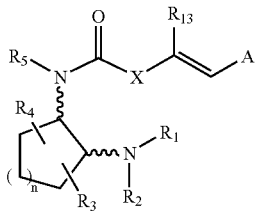

wherein, independently at each occurrence, n is selected from 1, 2, 3 and 4;

X is a direct bond,

Y is a direct bond;

$R_{13}$ is selected from hydrogen, $C_1$–$C_6$alkyl, $C_3$–$C_8$cycloalkyl, aryl, and benzyl;

$R_1$ and $R_2$ are taken together with the nitrogen atom to which they are directly attached in formula (I) to form a morpholinyl ring and where any one or more of the carbon ring atoms in the morpholinyl ring may be substituted with one or two substituents selected from hydrogen, hydroxy, $C_1$–$C_3$hydroxyalkyl, oxo, $C_2$–$C_4$acyl, $C_1$–$C_3$alkyl, $C_2$–$C_4$alkylcarboxy, $C_1$–$C_3$alkoxy, $C_1$–$C_{20}$alkanoyloxy, or may be substituted to form a spiro five- or six-membered heterocyclic ring containing one or two heteroatoms selected from oxygen and sulfur; and any two adjacent carbon ring atoms in the morpholinyl ring may be fused to a $C_3$–$C_8$carbocyclic ring;

$R_3$ and $R_4$ are independently attached to the cycloalkyl ring shown in formula (I) at other than the 1 and 2 positions and are independently selected from hydrogen, hydroxy, $C_1$–$C_6$alkyl, and $C_1$–$C_6$alkoxy;

$R_5$ is hydrogen, $C_1$–$C_6$alkyl, aryl and benzyl; and

A is selected from $C_5$–$C_{12}$alkyl, a $C_3$–$C_{13}$carbocyclic ring, and a ring system of formulae (III):

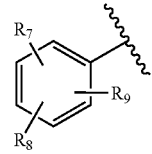

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, aryl and $N(R_{15},R_{16})$ where $R_{15}$ and $R_{16}$ are independently selected from hydrogen, acetyl, methanesulfonyl, and $C_1$–$C_6$alkyl;

including isolated enantiomeric, diastereomeric and geometric isomers thereof, and mixtures thereof.

2. A mixture of (1R,2R)-N-[2-(4-morpholinyl)cyclohexyl]-3,4-dichlorocinnamide monohydrochloride and (1S,2S)-N-[2-(4-morpholinyl)cyclohexyl]-3,4-dichlorocinnamide monohydrochloride, and pharmaceutically acceptable salts and solvates thereof.

3. A composition comprising a pharmaceutically acceptable carrier, excipient or diluent and a compound according to claim 1 or claim 2.

4. A pharmaceutical composition comprising a pharmaceutically acceptable carrier, diluent, or excipient and a therapeutically effective amount of a compound according to claim 1 or claim 2.

5. A pharmaceutical composition comprising a pharmaceutically acceptable carrier, diluent, or excipient and an amount of a compound effective to provide therapy for arrhythmia in a warm-blooded animal, wherein the compound is a compound according to claim 1 or claim 2.

6. A compound selected from the group consisting of (1R,2R)-N-[2-(4-morpholinyl)cyclohexyl]-3,4-dichlorocinnamide monohydrochloride and (1S,2S)-N-[2-(4-morpholinyl)cyclohexyl]-3,4-dichlorocinnamide monohydrochloride, and pharmaceutically acceptable salts and solvates of any of the foregoing.

* * * * *

UNITED STATES PATENT AND TRADEMARK OFFICE
CERTIFICATE OF CORRECTION

PATENT NO. : 7,053,087 B1
APPLICATION NO. : 09/914884
DATED : May 30, 2006
INVENTOR(S) : Gregory N. Beatch et al.

It is certified that error appears in the above-identified patent and that said Letters Patent is hereby corrected as shown below:

Title Page
Item (54) should read as --AMINOCYCLOALKYL CINNAMIDE COMPOUNDS FOR ARRHYTHIMIA AND AS ANALGESICS AND ANESTHETICS--

Column 35
Line 25, delete "Y is a direct bond;"

Signed and Sealed this

Seventeenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 7,053,087 B1 Page 1 of 1
APPLICATION NO. : 09/914884
DATED : May 30, 2006
INVENTOR(S) : Gregory N. Beatch et al.

It is certified that error appears in the above-identified patent and that said Letters Patent is hereby corrected as shown below:

<u>Title Page</u>
Item (54) should read as --AMINOCYCLOALKYL CINNAMIDE COMPOUNDS FOR ARRHYTHMIA AND AS ANALGESICS AND ANESTHETICS--

<u>Column 35</u>
Line 25, delete "Y is a direct bond;"

Signed and Sealed this

Twelfth Day of December, 2006

JON W. DUDAS
*Director of the United States Patent and Trademark Office*